(12) United States Patent
Wakai et al.

(10) Patent No.: US 7,583,781 B2
(45) Date of Patent: Sep. 1, 2009

(54) X-RAY CT APPARATUS AND METHOD OF CONTROLLING THE SAME

(75) Inventors: Misako Wakai, Nasushiobara (JP); Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/533,946

(22) Filed: Sep. 21, 2006

(65) Prior Publication Data

US 2007/0064864 A1 Mar. 22, 2007

(30) Foreign Application Priority Data

Sep. 22, 2005 (JP) ............................ 2005-276110

(51) Int. Cl.
*A61B 6/00* (2006.01)
(52) U.S. Cl. .......................................... 378/4; 378/147
(58) Field of Classification Search .................... 378/4, 378/55, 147, 901
See application file for complete search history.

(56) References Cited

U.S. PATENT DOCUMENTS

| 5,032,990 | A | * | 7/1991 | Eberhard et al. ............... 378/4 |
| 5,412,702 | A | | 5/1995 | Sata |
| 5,828,718 | A | * | 10/1998 | Ruth et al. ..................... 378/19 |
| 6,445,761 | B1 | * | 9/2002 | Miyazaki et al. ............... 378/8 |
| 6,778,628 | B2 | * | 8/2004 | Yamazaki et al. .............. 378/8 |
| 6,834,097 | B2 | * | 12/2004 | Yamazaki ..................... 378/19 |
| 6,922,457 | B2 | * | 7/2005 | Nagata et al. ................. 378/19 |
| 6,990,175 | B2 | * | 1/2006 | Nakashima et al. ........... 378/65 |
| 7,113,569 | B2 | * | 9/2006 | Okumura et al. ............. 378/150 |
| 7,123,691 | B2 | * | 10/2006 | Nakanishi et al. ........... 378/165 |
| 7,263,156 | B2 | * | 8/2007 | Roberts et al. ................ 378/14 |
| 2001/0031032 | A1 | * | 10/2001 | Proksa ......................... 378/15 |
| 2002/0191737 | A1 | * | 12/2002 | Tanigawa ..................... 378/19 |
| 2003/0123604 | A1 | * | 7/2003 | Edic et al. ..................... 378/19 |
| 2004/0066876 | A1 | * | 4/2004 | Tam ............................... 378/4 |
| 2005/0008115 | A1 | * | 1/2005 | Tsukagoshi ..................... 378/4 |
| 2005/0053188 | A1 | * | 3/2005 | Gohno ........................ 378/15 |
| 2007/0081624 | A1 | * | 4/2007 | Nabatame .................... 378/19 |

FOREIGN PATENT DOCUMENTS

JP 5-192327 8/1993

* cited by examiner

*Primary Examiner*—Edward J Glick
*Assistant Examiner*—Alexander H Taningco
(74) *Attorney, Agent, or Firm*—Oblon, Spivak, McClelland, Maier & Neustadt, P.C.

(57) ABSTRACT

An X-ray CT apparatus includes an X-ray detector that is asymmetrically disposed with respect to an irradiation axis of an X-ray and first and second ends that are disposed close to and far from the irradiation axis of the X-ray, respectively. When a scanogram of an object is imaged in one direction only, a part of the object at the first end is missed. Accordingly, scanograms are imaged in first and second directions that are opposite to each other, and then the imaged scanograms are superimposed. The superimposed scanogram is used as an image for setting a scanning range. According to this configuration, although a scanogram is produced by an X-ray CT apparatus having an asymmetrically disposed X-ray detector, it is possible to produce a desired projection data by obtaining scanogram data in the opposite two directions and combining each data. As a result, the accuracy in setting of a scanning position is not deteriorated.

8 Claims, 13 Drawing Sheets

| No. | START | START POSITION | STOP POSITION | SCAN MODE | NUMBER OF SCAN | kV | mA | SCAN SPEED | RECONSTRUCT-ING MODE | FOV | HELICAL PITCH |
|---|---|---|---|---|---|---|---|---|---|---|---|
| 1 | r | -978.5 | -1086.5 | HELICAL | 10 | 120 | | Auto | | 282.5 | 4.0 |
| | | | | | | | | Others | High Quality | | |
| | | | | | | | | 50 | Low Dose | | |
| | | | | | | | | 100 | SD5.0 | | |
| | | | | | | | | 150 | SD6.0 | | |
| | | | | | | | | 200 | SD7.0 | | |
| | | | | | | | | 250 | SD8.0 | | |
| | | | | | | | | 300 | SD9.0 | | |
| | | | | | | | | 300 | SD10.0 | | |

X-RAY CT APPARATUS AND METHOD OF CONTROLLING THE SAME

BACKGROUND OF THE INVENTION

1. Field of the Invention

The present invention relates to an X-ray CT apparatus that can produce a desired scanogram without a missed portion (an image for setting a scanning range), although a detector is asymmetrically positioned with respect to a line connecting the focus and the rotational center of an X-ray tube.

2. Description of the Related Art

Figure 1:
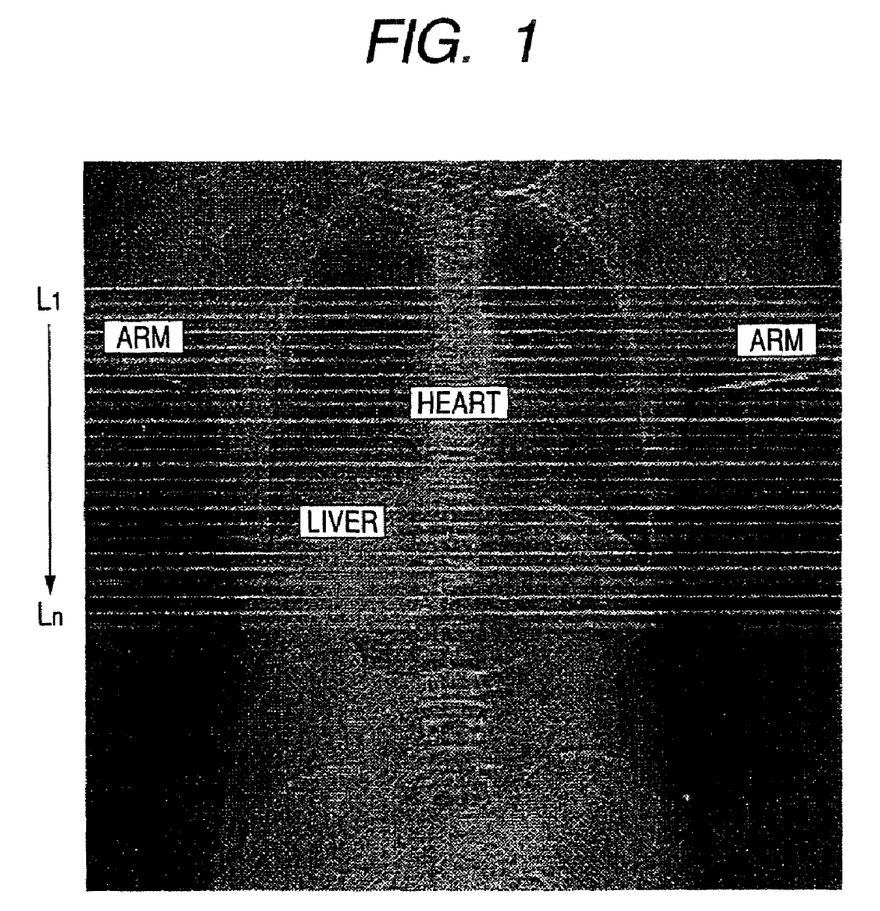
FIG. 1 is a scanogram imaged by a conventional X-ray CT apparatus.

In general, when the inside of an object is imaged by an X-ray CT apparatus, first, the X-ray CT apparatus produces an image for setting a scanning range (e.g. JP-A-192327). The image for setting a scanning range is a scanogram, i.e. a radioscopic image for a predetermined range of the object. In the imaging of the inside of the object, a position where a tomogram is imaged is determined on the basis of the scanogram. Accordingly, the X-ray CT apparatus obtains a tomogram by scanning the determined position using X-rays. When obtaining a scanogram, the X-ray CT apparatus irradiates X-rays onto the object, while not rotating the X-ray tube and moving a top board of a bed where the object is placed in the body axial direction of the object. A scanogram 30 as shown in FIG. 1 is produced on the basis of projection data obtained by the X-ray irradiation and displayed on a screen of a display.

In the determination of positions for imaging a tomogram, the positions for imaging a tomogram are set on the scanogram. The set positions are, for example, indicated by lines $L_1, L_2, \ldots L_n$ as shown in FIG. 1. During scanning for obtaining a tomogram, the top board of the bed where the object is placed returns to the initial position after the imaging for producing a scanogram is finished and moves again thereafter. The X-ray tube is disposed to the above positions $L_1$ to $L_n$ by moving the top board of the bed. The X-ray tube irradiates X-rays, rotating around the object. Tomograms for the object at the positions $L_1$ to $L_n$ are obtained as images based on the projection data obtained by the X-ray irradiation.

In recent years, some of X-ray detectors for X-ray CT apparatuses tend to be asymmetrically disposed with respect to an irradiation axis of an X-ray extending from the focus of the X-ray tube through the rotational centers of the X-ray tube and X-ray detector. The asymmetrically disposed X-ray detector is formed such that the right and left thereof are asymmetric with respect to the irradiation axis of the X-ray irradiated from the X-ray tube, and the edges are separated into an end closer to and the other end farther from the irradiation axis.

However, when the scanogram is imaged the an X-ray CT apparatus having an asymmetrically disposed X-ray detector, because the right and the left of the X-ray detector collecting the X-rays transmitted through the object are asymmetrical to each other with respect to the irradiation axis, a missed portion of the imaging region of the object is generated in a collection FOV (Field Of View).

SUMMARY OF THE INVENTION

Accordingly, it is an object of the present invention to provide an X-ray CT apparatus that can obtain a scanogram without a missed portion, although it includes an asymmetrically disposed X-ray detector.

According to a first embodiment of the invention, an X-ray CT apparatus includes an X-ray tube and an X-ray detector that has first and second ends in a direction perpendicular to the body axis of an object and the X-ray irradiation axis, the first end being closer to the X-ray irradiation axis than the second end and the second end being farther from the X-ray irradiation axis than the first end. The X-ray CT apparatus moves the X-ray tube by a first rotational angle and obtains projection data in a first direction, and then moves the X-ray tube by a second rotational angle and obtains projection data in a second direction. Subsequently, the X-ray CT apparatus superimposes the projection data corresponding to the first and second directions and produces an image for setting a scanning range.

Further, according to the first embodiment of the invention, although a scanogram is produced by an X-ray CT apparatus having an asymmetrically disposed X-ray detector, a desired projection data (scanogram data) can be produced by obtaining projection data in two directions and combining each projection data. Accordingly, the accuracy in setting of a scanning position can be secured.

Meanwhile, according to a second embodiment of the invention, an X-ray CT apparatus includes an X-ray tube, an X-ray detector that has first and second ends in a direction perpendicular to the body axis of an object and the X-ray irradiation axis, the first end being closer to the X-ray irradiation axis than the second end and the second end being farther from the X-ray irradiation axis than the first end; and a projector that shows the X-ray irradiation regions at the first and second ends.

Further, according to the second embodiment of the invention, when a scanogram is imaged in one direction within an X-ray irradiation range lightened by the projector, because the X-ray CT apparatus can discriminate in advance whether a part of an object is excluded from the range, the scanogram is not repeatedly imaged, thus the object is not unnecessarily exposed to the X-rays.

BRIEF DESCRIPTION OF THE DRAWINGS

FIG. 4 illustrates projection by a laser projector in an X-ray CT apparatus, in which

FIG. 7 shows mono directional scanogram data to be processed by an image processor of an X-ray CT apparatus, in which

FIG. 8 is scanogram data in the other direction processed by an X-ray CT apparatus.

DESCRIPTION OF THE PREFERRED EMBODIMENTS

An X-ray CT apparatus according to an embodiment of the invention will be described hereafter. The same reference numerals are given to the components having the same functions and configurations herein, and some components are repeatedly described, only if needed.

Although a variety of types of X-ray CT apparatuses are known, such as a ROTATE/ROTATE type in which X-ray tubes and X-ray detectors rotate around an object as a unit and a STATIONARY/ROTATE type in which several detecting elements are disposed in a ring shape and only an X-ray tube rotates around an object, the present invention is applicable to all types of X-ray CT apparatuses. However, preferred embodiments of the present invention are described herein in relation to the ROTATE/ROTATE type that is currently the mainstream of X-ray CT apparatuses.

In order to reconstruct tomogram data of a slice, projection data obtained during one rotation, about 360°, around an object is required, or according to a half scan method, projection data obtained by 180°+a view angle is required. The present invention is also applicable to both reconstructing methods. A case in which a tomogram is reconstructed from projection data for about 360° C. will be described herein.

The two known mechanism for converting irradiated X-rays into electric charges is an indirect converting type in which an X-ray is converted into light by a fluorescent body such as a scintillator and then the light is converted into an electric charge by a photoelectric transducer such as a photodiode, and a direct converting type using a photoconductive phenomenon that electron-hole pairs are generated by X-rays and moves to electrodes in a semiconductor. An X-ray detector may be any one of the types, but is described herein in relation to the indirect converting type.

In recent years, a multi-tube spherical X-ray CT apparatus that has a plurality of pairs of X-ray tubes and X-ray detectors mounted on a rotating frame has been produced and peripheral technologies have progressed accordingly. The present invention is applicable to conventional single-tube spherical X-ray apparatuses and multi-tube spherical X-ray CT apparatuses. However, a single-tube spherical apparatus is described herein by way of an example.

Configuration

Figure 2:
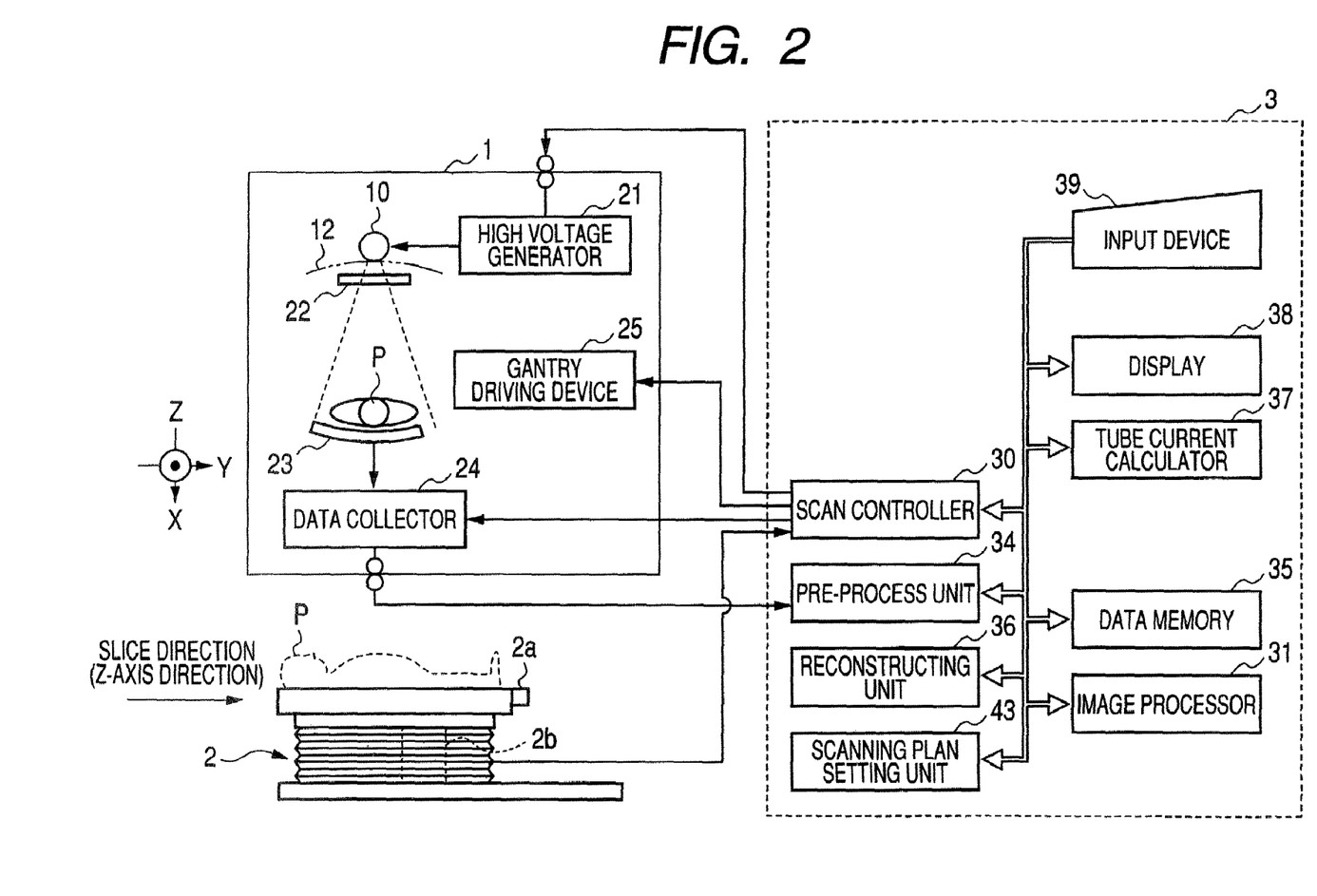
FIG. 2 is a block diagram showing a schematic configuration of an X-ray CT apparatus.

FIG. 2 is a block diagram showing the configuration of an X-ray CT apparatus according to an embodiment of the invention. As shown in FIG. 2, an X-ray CT apparatus includes a gantry 1 and a calculating system 3. The gantry 1 includes an X-ray tube 10 and an X-ray detector 23. The X-ray tube 10 and the X-ray detector 23 are mounted on a ring-shaped rotating frame 12. The rotating frame 12 is rotated about the z-axis by a gantry-driving device 25.

An opening is formed at the central portion of the rotating frame 12. An object P who is disposed on a top board 2a of a bed 2 is inserted into the opening. A collimator 22 is disposed between the X-ray tube 10 and the opening. The collimator 22 is made of a material such as plumbum, tungsten or etc. so as to block an X-ray, and narrows the irradiation range of X-rays. A top board driving unit 2b is provided to the bed 2 to longitudinally move the top board 2a (parallel to the rotational axis). The top board driving unit 2b includes a top board position detector, such as a rotary encoder, to detect the position of the top board 2a.

A tube voltage is applied between an anode and a cathode of the X-ray tube 10 by a high voltage generator 21. A filament current is supplied from the high voltage generator 21 to a filament of the X-ray tube 10. X-rays are generated by applying a high voltage or supplying a filament current.

The X-ray detector 23 includes, for example, a 0.5 mm×0.5 mm isotropic two-dimensional array of a plurality of detecting elements 26. For example, 916 pieces of detecting elements are arrayed at 0.5 mm pitch in the channel direction. For example, 40 lows (segment) of 916 pieces of detecting elements are arrayed at 0.5 mm pitch in the slice direction.

Figure 3:
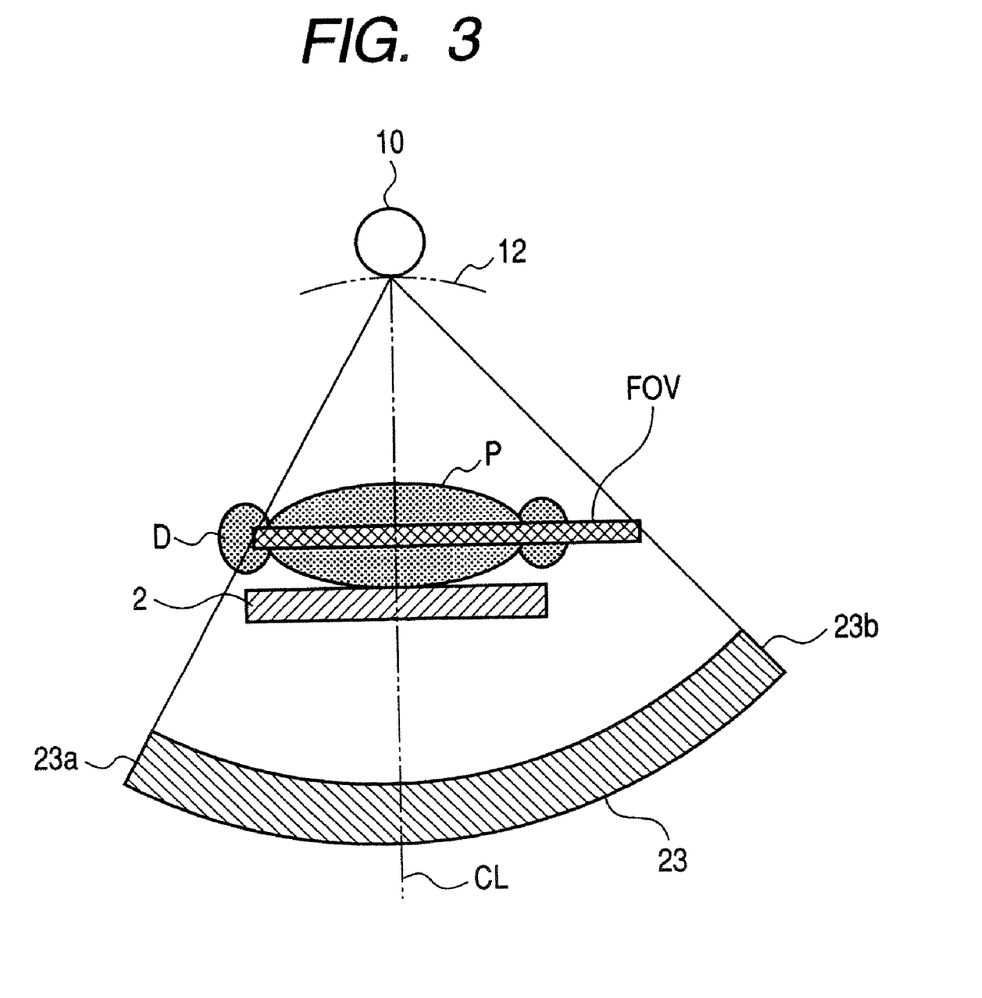
FIG. 3 is a block diagram showing a configuration of a gantry in an X-ray CT apparatus.

The X-ray detector 23 is, as shown in FIG. 3, positioned asymmetrically with respect to an irradiation axis CL that connects the focus of the X-ray tube 10 and the rotational center of the X-ray tube 10 and the X-ray detector 23. In the asymmetrically positioned X-ray detector 23, a first end 23a is closer to the irradiation axis CL than the other end, i.e. second end 23b in the direction perpendicular to the body axis and the irradiation axis CL. In other words, the second end 23b is farther from the irradiation axis CL than the first end 23a.

When an image for setting a scanning range in which a portion of an object P is not included within FOV in a direction is detected using the asymmetrically positioned X-ray detector 23, the obtained scanogram data is outputted as an image excluding a missed portion D of the object P at the first end 23a.

Figure 6A:
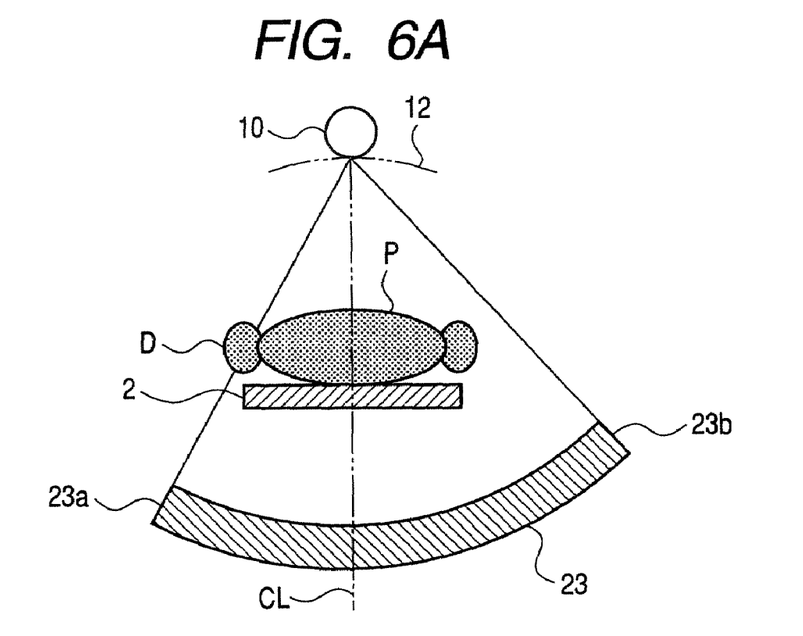
FIG. 6 shows a range that can be imaged by an X-ray CT apparatus so as to determine a position.
Figure 6B:
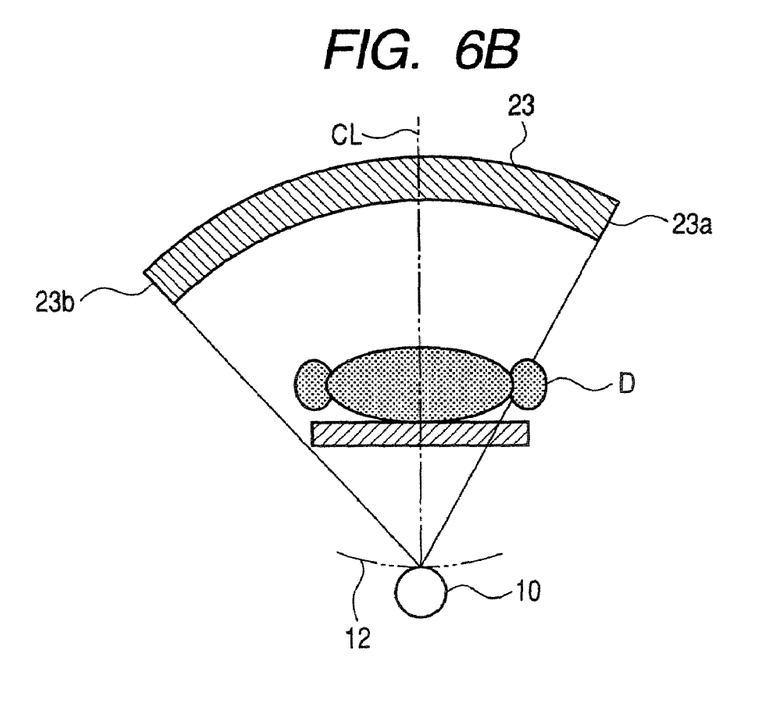

According to the X-ray CT apparatus according to an embodiment of the invention, the rotating frame 12 is rotated by a gantry driving device 25 controlled by a scan controller 30, so that, as shown in FIG. 3, scanogram data is obtained in a direction (see FIG. 6A) and the opposite direction (see FIG. 6B). The scanogram data in both directions are superimposed and scanogram including the missed portion D is generated (described below in detail).

A data collector 24, generally called as a DAS (Data Acquisition System) converts signals in each channel outputted from the X-ray detector 23 into voltage signals and amplifies the voltage signals, and then converts the amplified signals into digital signals. The digital signals, also called as raw data, are supplied to a calculating system 3 provided outside the gantry 1.

A pre-process unit 34 of the calculating system 3 corrects the raw data outputted from the data collector 26, such as sensitivity correction, and outputs the corrected data as projection data. The projection data is transmitted to a data memory 35 of the calculating system 3 to be stored.

The calculating system 3 includes, in addition to the pre-process unit 34 and the memory 35, an input device 39 including a keyboard or a mouse, a display 38, a scan controller 30, an image processor 31, a reconstructing unit 36, a scanning plan setting unit 43, and a tube current calculator 37.

The reconstructing unit 36 is capable of selectively using a variety of reconstructing processes of a typical fan beam method (also called as divergent ray convolution backprojection method), a helical interpolation method, a feldkamp method, and a cone beam reconstructing method.

The helical interpolation method is a reconstructing method that may be used in combination with the fan beam reconstructing method, and obtains projection data on a reconstructing surface, for example, from projection data corresponding to two rotations by interpolation. The feldkamp method is, as the cone beam method, a reconstructing method used when a projection ray crosses a constructing surface, and an approximate reconstructing method that processes fan projection beams while convoluting and an inverse projections according to rays during scanning, assuming that a cone angle is small. The cone beam reconstructing method has fewer errors in cone angles than the feldkamp method and corrects projection data depending on the angle of a ray against a reconstructing surface.

The image processor 31 generates one desired scanogram data by superimposing two scanogram data obtained by irradiating X-rays onto an object P in two opposite directions. In the superimposing of two scanogram data, for example, scanogram data at the second end 23b, which is far from the irradiation axis CL, is extracted from each of the two scanogram data and the extracted two scanogram data are superimposed with the irradiation axis CL as a center.

In the X-ray detector 23 according to the present embodiment, the missed portion D occurs at the first end 23a close to the irradiation axis CL. In order to supplement the scanogram data of the missed portion D, in the scanogram data obtained by irradiating in the opposite directions, the scanogram data at the end where the missed portion D appears is used.

While superimposing the scanogram data, a magnification of each scanogram maybe adjusted so that the relative positions of the object P (spatial coordinates) to the X-ray tube 10 and the X-ray detector 23 are substantially the same. The relative positions of the object P (spatial coordinates) to the X-ray tube 10 and the X-ray detector 23 may be determined on the basis of the positional information of the gantry 2 (in more detail, the distance between the top board 2a of the gantry 2 and the X-ray detector 23) where the object P is placed.

The scanning plan setting unit 43 has a function required to guide an operator so as to select a scanning plan. For example, the scanning plan setting unit 43 provides a screen on which an operator can input various items such as patient information, diagnostic object, and a part to be diagnosed, etc., and shows the screen through a display 38.

The tube current calculator 37 calculates the tube current supplied to the X-ray tube 10 when a scanning plan is set.

Figure 4A:
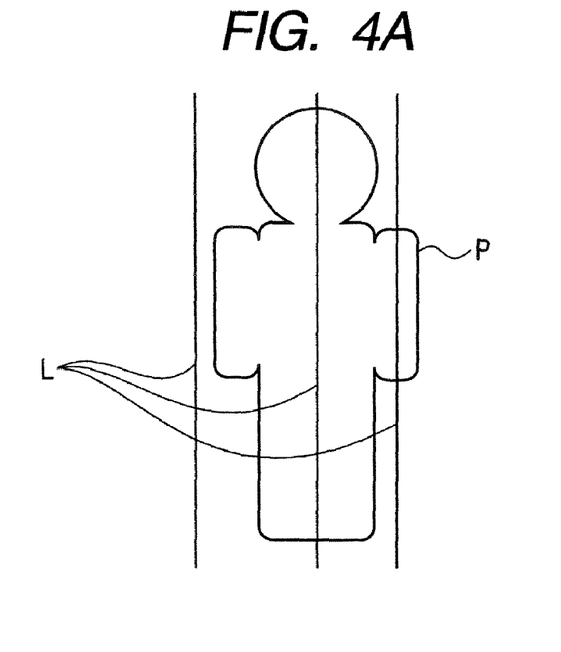
FIG. 4A illustrates projection according to an embodiment of the present invention.
Figure 4B:
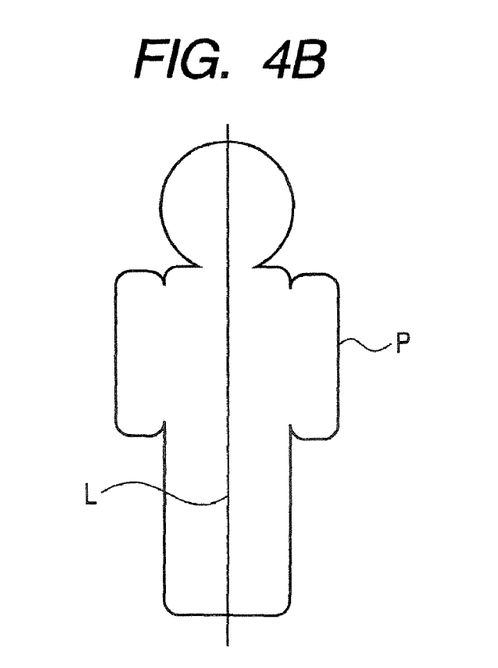
FIG. 4B illustrates conventional projection.

In the X-ray CT apparatus according to the present embodiment, a laser indicator is mounted to the gantry 1. The laser indicator indicates a range that can be imaged when a scanogram is imaged by the asymmetrically positioned X-ray detector 23 in one direction only, and irradiates a laser from the position of the X-ray tube 10 toward the first and second ends 23a and 23b of the X-ray detector 23. When an object P is placed on the bed 2, the laser indicator irradiates a laser and, for example, as shown in FIG. 4A, marks lines, which indicates the positions of the first and second ends 23a and 23b, on the surface of the object P or the bed 2. Conventional laser indicators mark a line L that indicates only the center in the upper direction (the front direction of the object P) and the left/right directions (the left and right directions of the object P placed on the bed 2) to help appropriately placing the object P about the irradiation axis CL of the X-ray tube 10 (see FIG. 4B).

Figure 5:
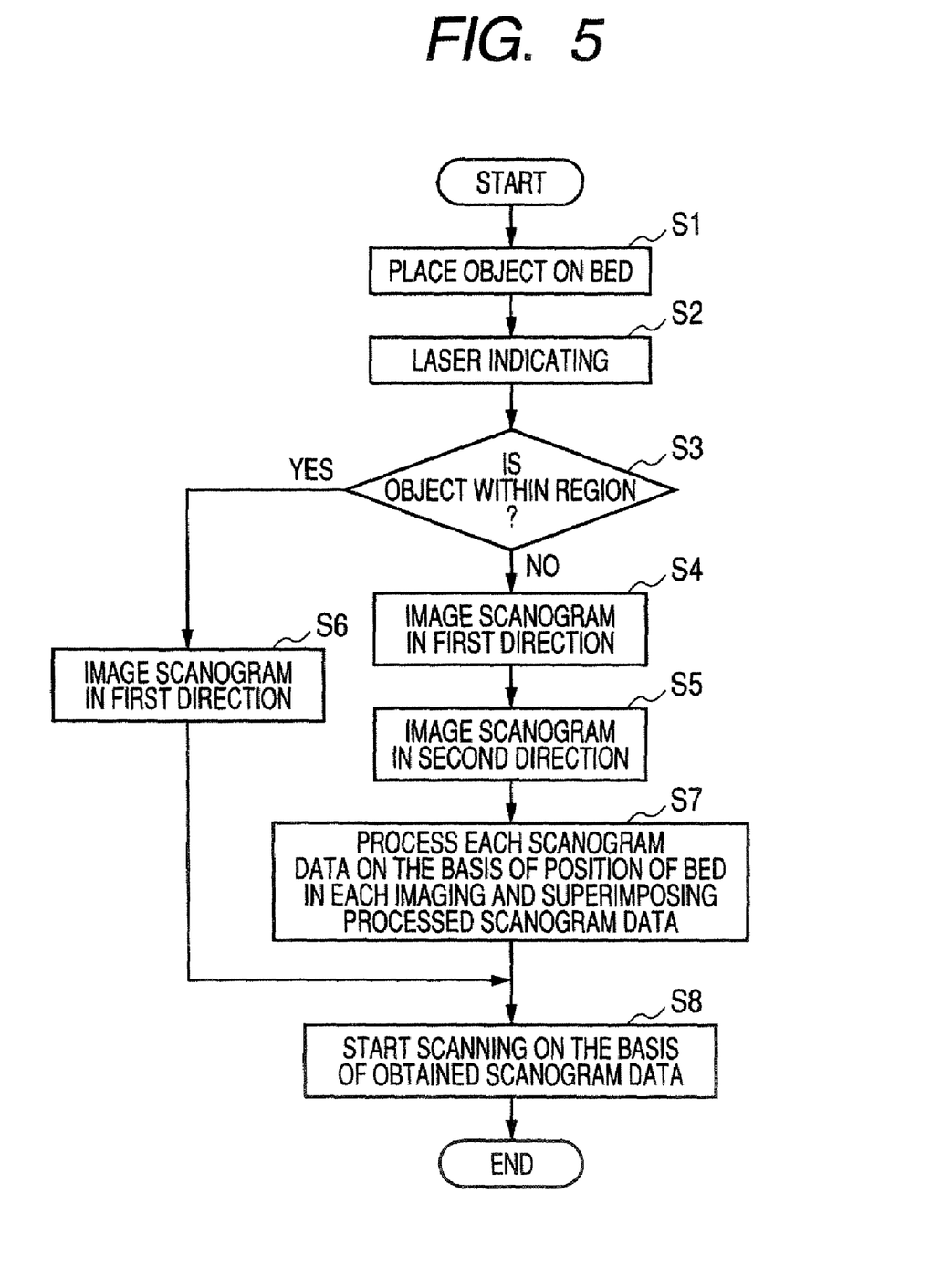
FIG. 5 is a flowchart showing an operation of a driving part of an X-ray CT apparatus.

FIG. 5 is a flowchart showing the flow of imaging a scanogram in the X-ray CT apparatus according to the present embodiment. As shown in FIG. 5, an object P is placed face up on the bed 2 (S1).

The laser indicator mounted to the gantry 1 indicates an imaging region when a scanogram is imaged in one direction only, using lasers (S2). The laser indicator irradiates lasers from the position of the X-ray tube 10 towards the first and second ends 23a and 23b and marks an imaging region on the surface of the object P where the laser is irradiated (see FIG. 4A).

When the entire object P is not included within the region between the two laser indicators (within FOV) (S3—No), an operator selects a mode "imaging scanograms in two directions" through the input device 39. The scan controller 30 receiving the selection of the mode "imaging scanograms in two directions" operates "to image scanograms in two directions".

On the other hand, the entire object P is included within the region between the two laser indicators (within the region that can be imaged) (S3—Yes), the operator selects a "normal" mode through the input device 39. The scan controller 30 receiving the selection of the "normal" mode operates the scanogram imaging in a first direction (e.g. upper direction (the facial direction of the object P placed face up on the bed 2)) (S6) and starts scanning on the basis of the obtained scanogram data (S8).

In the mode "imaging scanograms in two directions", first, as shown in FIG. 6A, the controller operates a scanogram imaging for a first position (S4). In the scanogram imaging for the first position, the scan controller 30 calibrates the X-ray tube 10 in the first direction and exposes the object to X-rays. According to the scanogram imaging in the first direction in the present embodiment, the scanogram imaging operates under the configuration that the X-ray tube 10 is disposed above the object P (above the face of the object P placed face up on the bed 2) and the X-ray detector 23 is disposed under the object P (under the back of the object placed face up on the bed 2) such that the object P is placed between them.

Subsequently, as shown in FIG. 6B, the scan controller 30 operates a scanogram imaging for a second position (S5). While imaging the scanogram in the second position, the controller 30 rotates the X-ray tube 10 and the X-ray detector 23 at 180° in the first direction with the object P as a center to calibrate the X-ray tube 10 in the second direction, and exposes the object P to X-rays. According to the scanogram imaging in the second direction in the present embodiment, the scanogram imaging operates under the configuration that the X-ray tube 10 is disposed under the object P (under the back of the object P placed face up on the bed 2) and the X-ray detector 23 is disposed above the object P (above the face of the object P placed face up on the bed 2).

After obtaining the scanogram data in the first and second directions, the image processor 31 processes each scanogram data on the basis of the positional information of the bed 2 in each imaging and superimposing of the data.

Figure 7A:
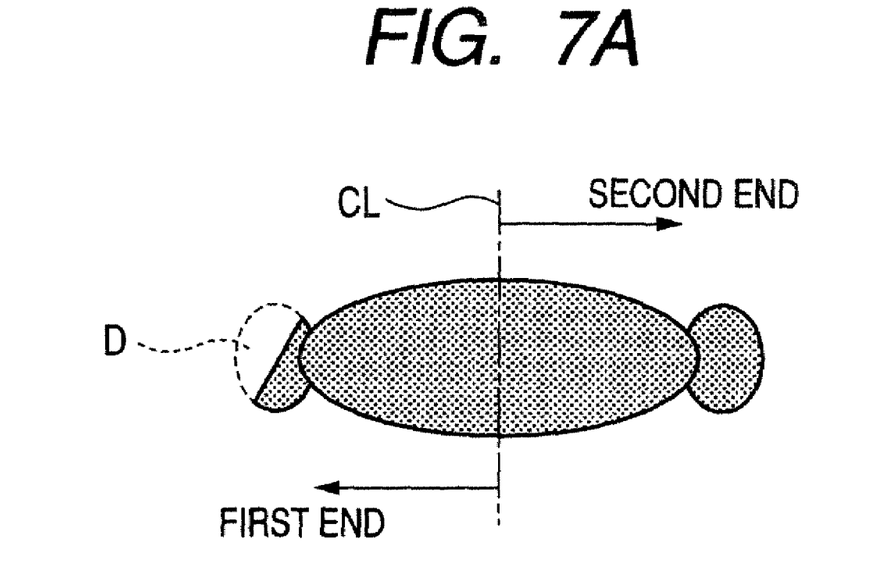
FIG. 7A is the scanogram data.
Figure 7B:
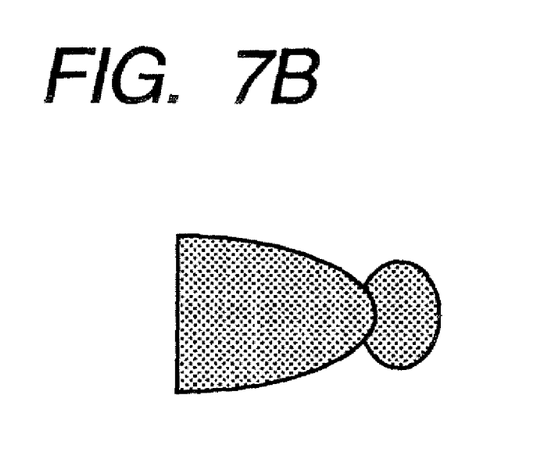
FIG. 7B is extracted scanogram data between an irradiation axis and a second end.
Figure 8A:
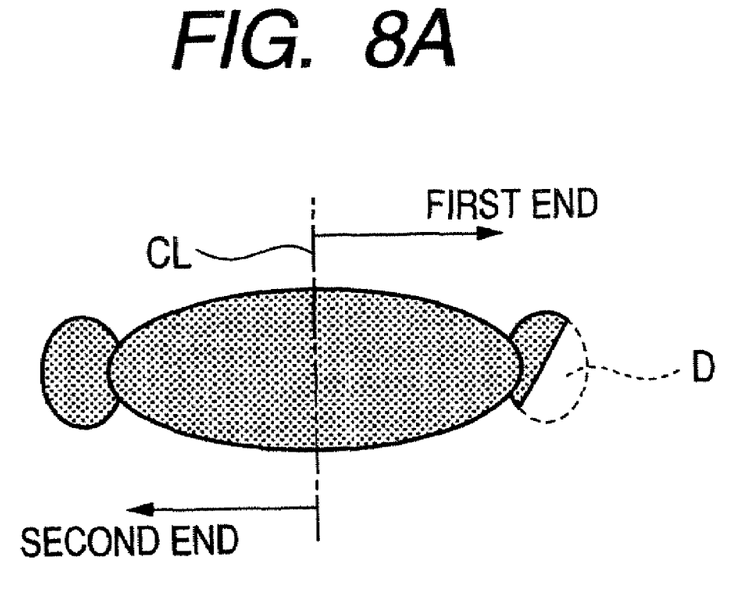
FIG. 8A is the scanogram data.
Figure 8B:
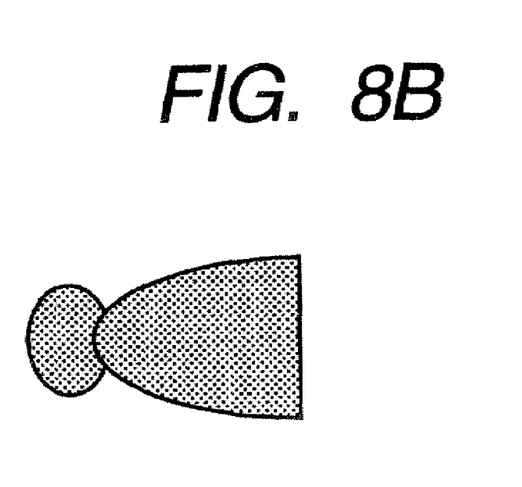
FIG. 8B is extracted scanogram data between the irradiation axis and the second end.

FIGS. 7a and 8a are examples of scanograms of the object P when the scanograms are imaged in the first and second directions. FIGS. 7b and 8b are views showing extracted portions out of the scanograms of the object P in the first and second directions by the image processor 31, respectively.

As shown in FIGS. 7a and 8a, the missed portion D appears at the first end 23a close to the irradiation axis CL for each direction. Accordingly, as schematically shown in FIGS. 7b and 8b, the image processor 31 extracts scanogram data between the irradiation axis CL and the second end 23b from the scanograms imaged in the first and second directions and superimposing the extracted data parallel with each other with the irradiation axis CL centered.

Before superimposing the data and when obtaining each scanogram data, the image processor 31 adjusts the size the image of the scanogram data on the basis of the positional signal of the top board transmitted from a top board position detector in the top board driving unit 2b of the bed 2 such that positional information of the bed 2 (in more detail, the distances from the top board 2a of the bed 2 and the X-ray detector 23) where the object P is placed are the same.

The superimposed scanogram data is stored in the data memory 36. The size adjustment implies a process that makes the image size of the scanogram data (the number of dots forming the image) uniform for any one of the first and second directions for the obtained scanogram data.

Therefore, even in the X-ray CT apparatus including the asymmetrically positioned X-ray detector 23, desired scanogram data without the missed portion D can be obtained by superimposing the portions at the second end 23b far from the irradiation axis CL of the scanogram data imaged in the two opposite directions.

Figure 9:
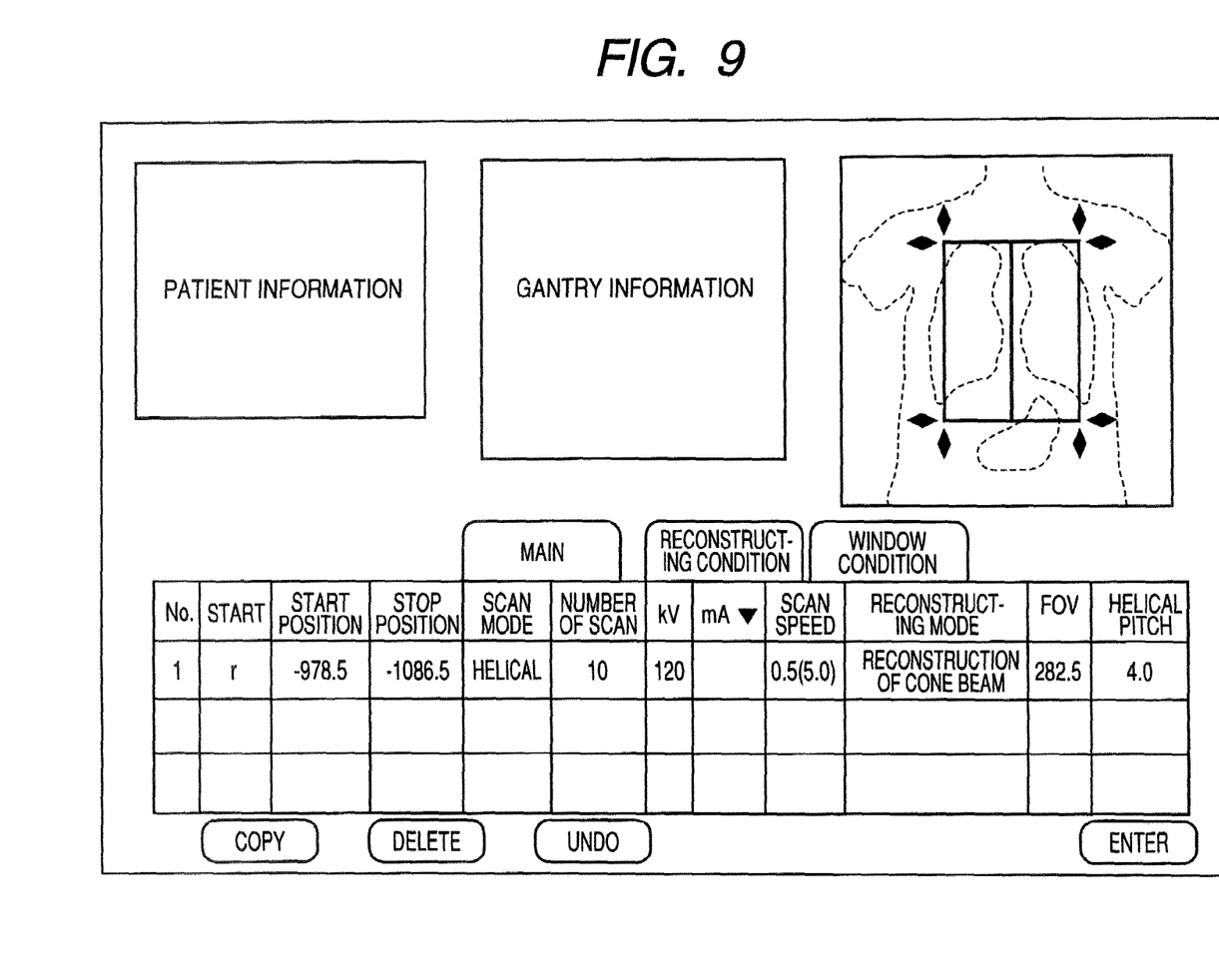
FIG. 9 shows an example of a scanning plan displayed by an X-ray CT apparatus.

In the X-ray CT apparatus, a scanning plan for a tomogram of an object is set using desired scanogram data without the missed portion D. FIG. 9 shows an example of a screen for setting a scanning plan. In the scanning plan screen, a patient information-displaying area Ea, a gantry information-displaying area Eb, and a scanogram-displaying area Ec are displayed at the upside and a scanning condition-displaying area Ed is displayed at the downside.

Patient information is displayed in the patient information-displaying area Ea, gantry information is displayed in the gantry information displaying area Eb, a scanogram is displayed in the scanogram-displaying area Ec, and a detailed scanning condition is displayed in the scanning condition-displaying area Ed.

The scanning condition includes a variety of items such as start and stop position items Ia and Ib of a helical scan that corresponds to an outline of a scanogram, a scan mode item Ic, a scan number item Id, a tube voltage (kV) item Ie, a tube current (mA) item If, a scan speed item Ig that represents a time required for one rotation of the X-ray tube 10 (the value in a parenthesis represents imaging time), a reconstructing mode item Ih, an imaging view (FOV) mode item Ii, and a helical pitch item Ij that represents a movement distance of the top board with the scan pitch.

Figure 10:
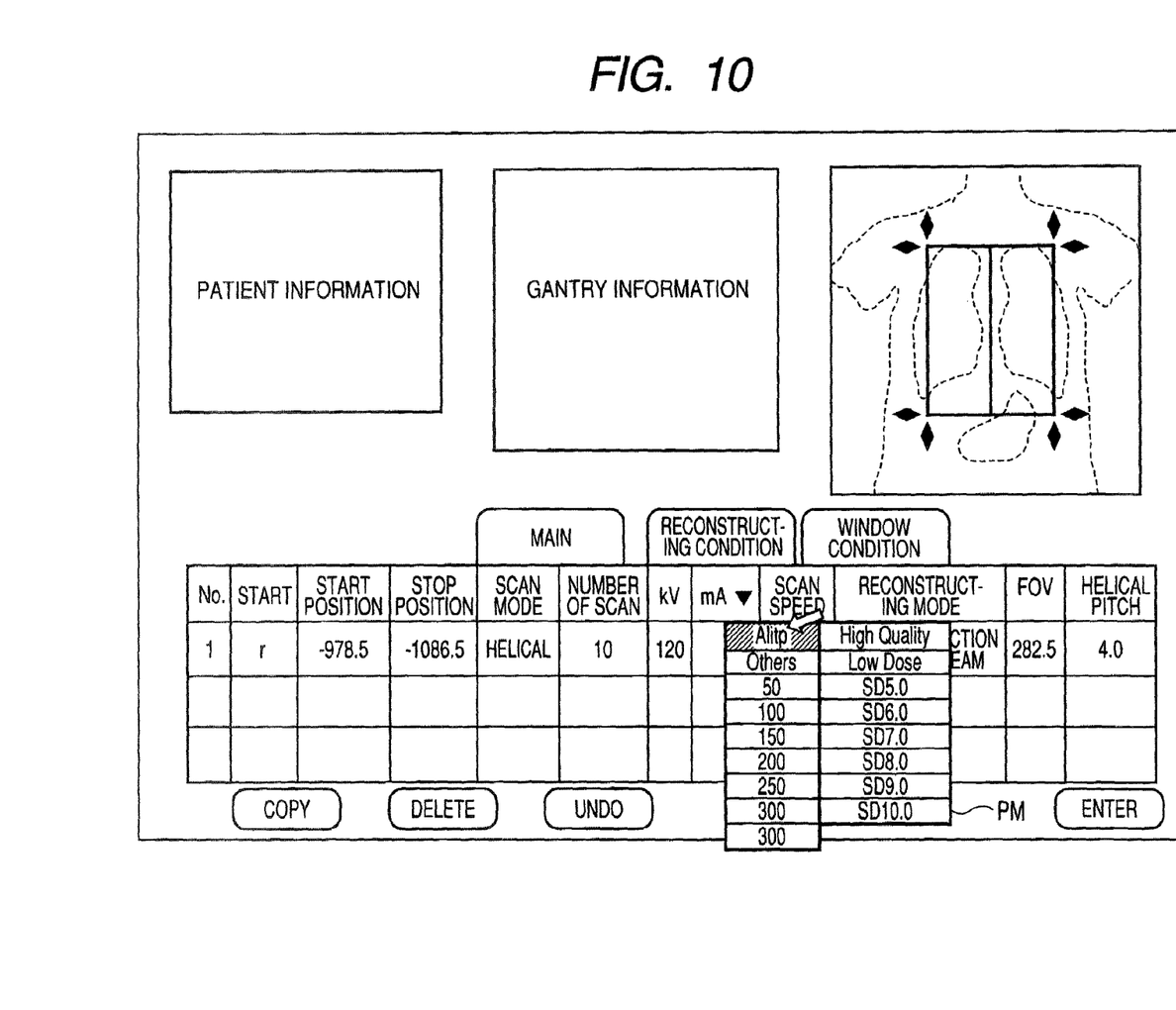
FIG. 10 shows a display with a pull-down menu to set tube current to a scanning plan displayed by an X-ray CT apparatus.

A box for directly inputting a value of tube current and a pull down menu PM are included in the tube current (mA) item If (see FIG. 10). A plurality of tube current values and "Auto" are included as an option of the pull down menu PM. The automatic setting of a tube current value is a function that when an operator sets an image SD that is an index representing the image quality, a tube current value required to achieve the set image SD is automatically set by the system.

Image noise is inevitably included in a reconstructed image. The image noise is generally represented as a standard deviation that implies a difference of CT values obtained when a uniform phantom is imaged. In general, the standard deviation representing image noise is called the image SD. When observing a reconstructed image and diagnosing, an operator needs to consider an image SD of the image to discriminate that, for example, shades in the image are noise or tumor. The image SD strongly tends to depend on the amount of transmitting X-rays that is determined by a function of a tube current and an object.

The tube current calculator 37 calculates a required tube current value to achieve the image SD selected by an operator, and computes a tube current value according to a predetermined computing formula, when required parameters are inputted. The tube current value is expressed by the following equation including a function of a water equivalent thickness DPb corresponding to the thickness of the object:

$$Ib=(SDa^2/SDinput^2)\times(mAs/t)\times PkV\times Psl\times PHP\times PFW\times PFC\times Pmode\times exp(-\mu(DPa-DPb)),$$

where, SDa: image SD of an image obtained by imaging and reconstructing a standard water phantom of the water equivalent thickness DPa as a function of standard tube current, standard tube voltage, standard imaging slice thickness, standard image slice thickness, and standard reconstruction, SDinput: image SD that an operator wants in a resultant image, mAs: time integrational value of a standard tube current (sec), t: scan speed (sec), PkV: coefficient corresponding to a tube voltage, Psl: coefficient corresponding to an imaging slice thickness, PHP: coefficient corresponding to a helical pitch, PFW: coefficient corresponding to the rate of image slice thickness relative to imaging slice thickness, PFC: coefficient corresponding to reconstructing function, Pmode: coefficient about normal mode or exposure-reducing mode of X-ray, μ: X-ray suction coefficient of water, DPa: standard water-equivalent thickness (mm), and DPb: water equivalent thickness corresponding to the object's thickness (mm).

The water equivalent thickness DPb corresponding to the object's thickness is induced from a scanogram obtained by superimposing scanograms imaged in the two directions and supplementing the missed portion D to the superimposed scanogram. The other parameters are obtained by the operator's input or stored in advance.

The water equivalent thickness DPb corresponding to the object's thickness is calculated through the following equation:

$$DPb=DW\times(SP/AW)^{1/2}$$

where, DW: diameter of water phantom that is approximate to the object's size,

SP: integration of pixel corresponding to one line in the slice direction that is obtained by imaging scanogram of the body, and AW: integrational value of pixel corresponding to one line that is obtained by imaging scanogram of water phantom.

The AW is obtained by imaging a scanogram of a cylindrical water phantom that is approximately the same as object's size and integrating the pixel values in one line in the scanogram. The SP is obtained by imaging a scanogram of the object and integrating the pixel values in one line in the scanogram. In the X-ray CT apparatus having the asymmetrically positioned X-ray detector 23, the scanograms used in the calculation of the AW and SP are obtained by imaging scanograms in two directions and superimposing the scanograms to supplement the missed portion D.

The water equivalent thickness DPb corresponding to the object's thickness is a converted value assuming that the object is water. When pixels in one line of a scanogram including the missed portion D is integrated, the water equivalent thickness DPb is calculated as the object's thickness of the portion where the missed portion D is removed. Meanwhile, according the present embodiment, a water equivalent thickness DPb precisely representing the entire thickness of the object can be calculated.

According to the X-ray CT apparatus, tube current is calculated on the basis of a scanogram obtained by imaging scanograms in two directions and superimposing them to supplement the missed portion D, while a scanning plan is set by an operator's input and a tomogram is made according to the scanning plan.

A first modification of the X-ray CT apparatus according to the above embodiment is described below.

Figure 11:
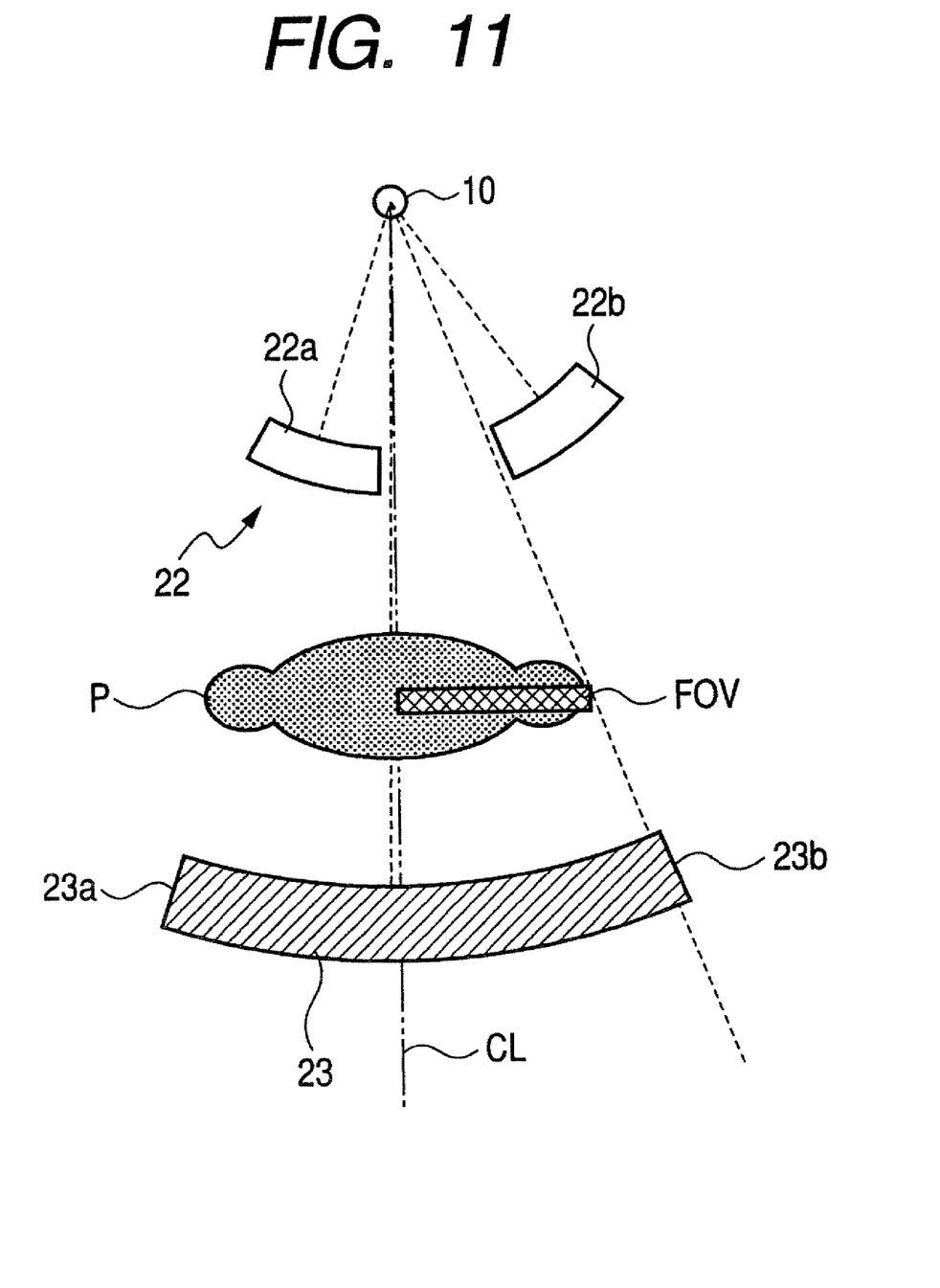
FIG. 11 shows a first modification when an X-ray CT apparatus images scanograms.

A modification of irradiating an X-ray when scanograms are imaged in two directions is shown in FIG. 11. In the above embodiment, the irradiation region is set from the first end 23a to the second end 23b to cross the irradiation axis CL. However, as shown in FIG. 11, when scanograms are imaged in two directions, each irradiation region may be set from the irradiation axis CL to the second end 23b far from the irradiation axis CL.

The collimator 22 includes several pairs of collimator blocks 22a and 22b that are disposed close to or far from the irradiation axis CL. The X-ray CT apparatus disposes the end of the collimator block 22a at the first end 23a to or close to the irradiation axis CL.

As a result, the collimator 22 narrows the region from the irradiation axis CL to the first end 23a and prevents X-rays from passing through the region. Therefore, X-rays cannot pass the region from the irradiation axis CL to the first end 23a. The X-ray CT apparatus images scanograms in two directions under the condition that the region from the irradiation axis CL of the collimator 22 to the first end 23a is blocked from X-rays. Only scanogram data from the irradiation axis CL to the second ends 23b is included in the imaged scanograms in the two directions. The scanograms in the two directions are superimposed with the irradiation axis CL as a center.

Accordingly, while the part of the object between the irradiation axis CL and the first end 23a close to the irradiation axis CL is not unnecessarily exposed to X-rays, a scanogram without the missed portion D can be achieved.

A second modification of the X-ray CT apparatus according to the above embodiment is described below. In the above embodiment, when scanograms obtained in the two directions are superimposed, the image size is adjusted on the basis of the positional information of the bed 2. However, the X-ray CT apparatus, after overlapping a part of the imaging region and imaging scanograms in two directions may adjust the image size through comparing the sizes of the parts of the object P within the overlapped imaging region.

Figure 12:
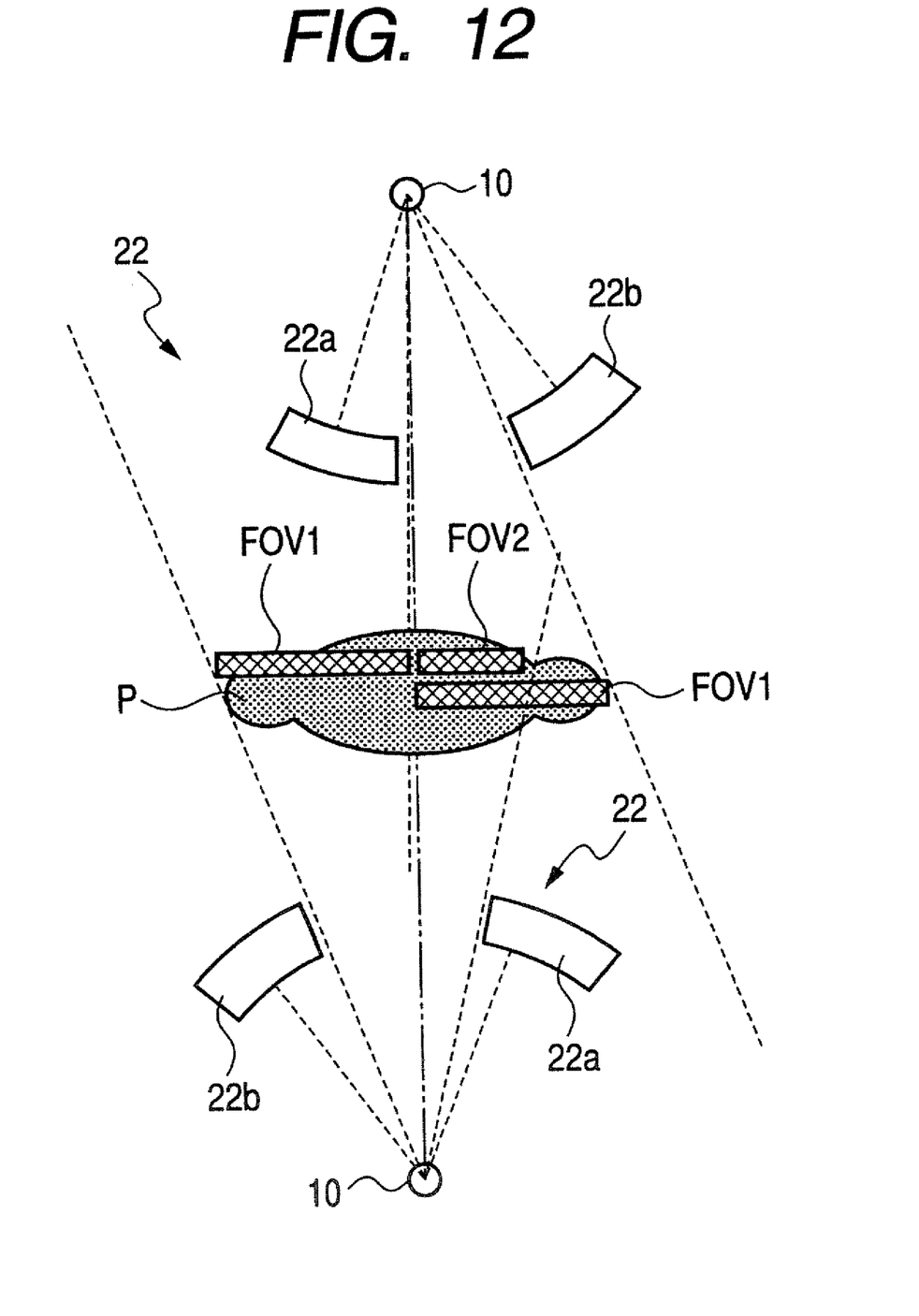
FIG. 12 shows a second modification when an X-ray CT apparatus images scanograms.

FIG. 12 schematically shows a state that scanograms are imaged in two directions after overlapping a part of the imaging region. As shown in FIG. 12, in the imaging of the scanogram in one direction, an irradiation region is set to a region FOV2 obtained by adding a predetermined region from the irradiation axis CL to the first end 23a to the region FOV1 from the irradiation axis CL to the second end 23b. In an imaging of a scanogram in the other direction, an irradiation region may be set to a region only from the irradiation axis CL to the second end 23b.

The collimator 22 is disposed such that an end of the collimator 22 is spaced from the irradiation axis CL at a predetermined distance. In this configuration, X-rays are irradiated onto the object P. The image processor 31 extracts the region FOV1 from the irradiation axis CL to the second end 23b as scanogram data to be superimposed, and also extracts the repeatedly imaged region FOV2 from each scanogram data.

Figure 13A:
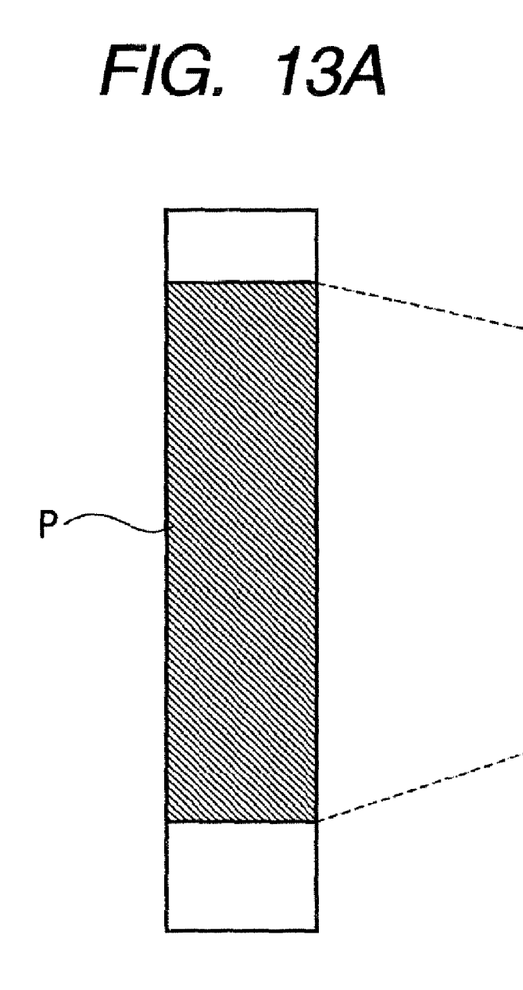
FIG. 13 shows scanogram data in an overlapping region of the scanogram imaged according to the second modification.
Figure 13B:
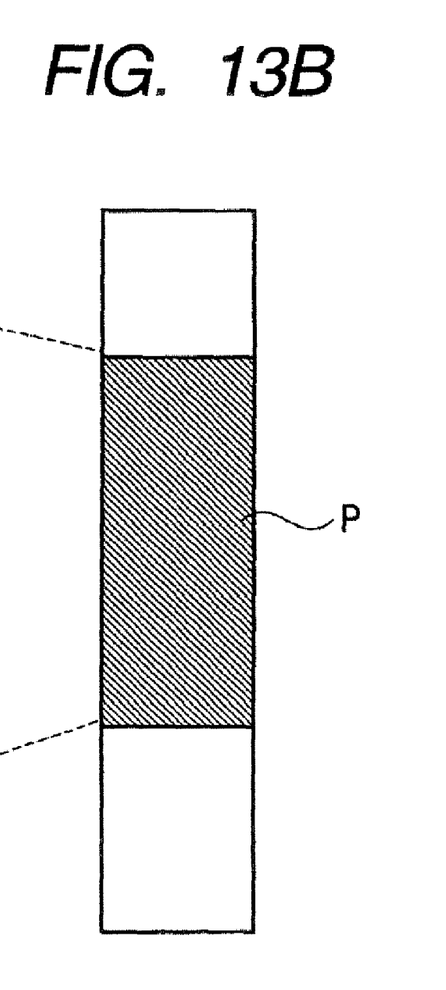

FIG. 13 schematically shows scanograms within the overlapping imaging region. (a) in FIG. 13 shows the overlapping region imaged in first direction, and (b) in FIG. 13 shows the overlapping region imaged in second direction. In the X-ray CT apparatus, when the rotational center of the X-ray tube 10 and the X-ray detector 23 deviates from the body axis of the object P, the sizes of the object P imaged in the scanogram in two directions are different and the image sizes need to be adjusted. When the rotational center and the body axis deviate from each other, the distances between the focus of the X-ray tube 10 when scanograms are imaged in each direction and the body axis are different. As the distances between the focus and the body axis are different, the focus of the object P changes and the size of the object imaged in the scanogram changes.

The image processor 31 calculates a magnification for one scanogram relative to the other by comparing the sizes of the object imaged in the scanograms obtained from the overlapped imaging region. After calculating the magnification, the image processor 31 multiplies the scanogram from the irradiation axis CL to the second end 23b by the inverse number of the obtained magnification to make the image sizes of the scanogram equal. After making the image sizes equal, the image processor 31 superimposes the scanograms with the irradiation axis CL as a center and produces a scanogram without the missed portion D.

As described above, according the embodiments of the invention, even though a scanogram is produced by an X-ray CT apparatus having asymmetrically disposed X-ray detector, imaging data (scanogram data) is obtained in two opposite directions and one desired imaging data can be produced, so that a setting accuracy of a scanning position is not decreased.

In imaging a tomogram, because a tube current value is determined by desired scanogram data without a missed portion, tube current that can accurately achieves the image quality (image SD) desired by an operator, so that the operator can obtain an image with predetermined image quality and does not need to repeatedly scan.

Further, because it may be possible to discriminate in advance whether a part of an object is missed when a scanogram is imaged in one direction using a laser projector that lightens an X-ray irradiation region at the first and second ends 23a and 23b, scanograms does not need to be repeatedly imaged and unnecessary exposure can be prevented.

In the imaging of scanograms in two directions, because scanograms are imaged within the region only between the irradiation axis CL and the second end 23b far from the irradiation axis CL and superimposed, the part of the object P between the irradiation axis CL and the first end 23a close to the irradiation axis CL is not unnecessarily exposed to X-rays and a resultant scanogram without the missed portion D can be obtained.

The present invention is not limited to the above embodiments and it will be apparent to those skilled in the art that various modifications and changes may be made thereto without departing from the scope and spirit of the invention. In other words, a variety of steps may be included in the above embodiments and a variety of modifications may be obtained by superimposing the disclosed plurality of components. For example, some of the components described in the above embodiment may be excluded.

What is claimed is:

1. An X-ray CT apparatus comprising:
   an X-ray tube;
   an X-ray detector that has first and second ends in a direction perpendicular to a body axis of an object and an X-ray irradiation axis, the first end being closer to the X-ray irradiation axis than the second end and the second end being farther from the X-ray irradiation axis than the first end;
   a scanning controller that obtains projection data in a first direction by moving the X-ray tube and the X-ray detector by a first rotational angle, wherein when the object is not within the range of X-ray detection from the first direction, the scanning controller obtains projection data in a second direction by moving the X-ray tube and the X-ray detector by a second rotational angle, respectively;

an image processor that superimposes the projection data corresponding to the first and second directions and produces an image for scan setting when the projection data in the second direction is obtained, wherein the image processor forms the image for scan setting from the projection data in the first direction when the projection data in the second direction is not obtained; and a scanner that sets a scanning plan based on the image for scan setting to scan the object based on the scanning plan.

2. The X-ray CT apparatus according to claim 1,
wherein the image processor superimposes the projection data obtained from the X-ray irradiation axis to the second end in the first direction and the projection data obtained from the X-ray irradiation axis to the second end in the second direction, and produces the image for scan setting.

3. The X-ray CT apparatus according to claim 2,
wherein the image processor makes display sizes the same on the basis of the positions of an object relative to the X-ray tube and the X-ray detector when each of the projection data in the first and second directions is obtained, and superimposes each projection data and produces the image for scan setting.

4. The X-ray CT apparatus according to claim 2, further comprising;
a collimator that narrows the irradiation region of X-rays irradiated from the X-ray tube,
wherein when X-rays are irradiated in the first and second directions, the collimator narrows the irradiation region down to the region from the X-ray irradiation axis to the second end.

5. The X-ray CT apparatus according to claim 2, further comprising:
a collimator that narrows the irradiation region of X-rays irradiated from the X-ray tube,
wherein when X-rays are irradiated in each of the first and second directions, the collimator narrows the irradiation region down to the region defined by adding a predetermined region expanding from the X-ray irradiation axis toward the first end to the region between the X-ray irradiation axis and the second end, and the image processor compares the object's display sizes from the projection data in the predetermined region obtained in the first and second directions, and superimposes the projection data obtained in the first and second directions after making the display sizes of the projection data equal on the basis of the compared result, and then produces the image for scan setting.

6. The X-ray CT apparatus according to claim 1,
wherein the image processor makes display sizes equal on the basis of the positions of an object relative to the rotational center of the X-ray tube and the X-ray detector when each of the projection data in the first and second directions is obtained, and superimposes each projection data and produces the image for scan setting.

7. The X-ray CT apparatus according to claim 1, further comprising:
a collimator that narrows an irradiation region of the X-rays irradiated from the X-ray tube,
wherein when X-rays are irradiated in the first and second directions, the collimator narrows the irradiation region down to the region from the X-ray irradiation axis to the second end.

8. The X-ray CT apparatus according to claim 1, further comprising;
a collimator that narrows the irradiation region of X-rays irradiated from the X-ray tube,
wherein the collimator narrows the irradiation region down to the region defined by adding a predetermined region expanding from the X-ray irradiation axis toward the first end to the region between the X-ray irradiation axis and the second end when X-rays are irradiated in each of the first and second directions, and the image processor compares the object's display sizes from the projection data in the predetermined region obtained in the first and second directions, and superimposes the projection data obtained in the first and second directions after making the display sizes of the projection data equal on the basis of the compared result, and then produces the image for scan setting.

* * * * *